(12) United States Patent
Hwang et al.

(10) Patent No.: US 7,875,237 B2
(45) Date of Patent: Jan. 25, 2011

(54) METHOD FOR MANUFACTURING DENTAL SCALER TIP USING POWDER INJECTION MOLDING PROCESS, MOLD USED THEREIN AND SCALER TIP MANUFACTURED BY THE SAME

(75) Inventors: Chul Jin Hwang, Bucheon-si (KR); Hyung Pil Park, Gunpo (KR); Young Bae Ko, Seoul (KR); Young Moo Heo, Seoul (KR); Jong Sun Kim, Goyang-si (KR)

(73) Assignee: Korea Institute of Industrial Technology, Chonan-si (KR)

( * ) Notice: Subject to any disclaimer, the term of this patent is extended or adjusted under 35 U.S.C. 154(b) by 0 days.

(21) Appl. No.: 11/912,797

(22) PCT Filed: Apr. 13, 2006

(86) PCT No.: PCT/KR2006/001367

§ 371 (c)(1),
(2), (4) Date: Oct. 26, 2007

(87) PCT Pub. No.: WO2006/115344

PCT Pub. Date: Nov. 2, 2006

(65) Prior Publication Data

US 2008/0254409 A1      Oct. 16, 2008

(30) Foreign Application Priority Data

Apr. 27, 2005      (KR) .................... 10-2005-0035138

(51) Int. Cl.
B22F 3/02      (2006.01)
(52) U.S. Cl. ................... 419/66; 419/5; 419/36; 419/38; 433/143; 433/119; 425/543
(58) Field of Classification Search .......... 419/66
See application file for complete search history.

(56) References Cited

U.S. PATENT DOCUMENTS

| 3,924,335 | A | * | 12/1975 | Balamuth et al. | ............ 433/119 |
| 5,531,597 | A | * | 7/1996 | Foulkes et al. | ............... 433/119 |
| 5,641,920 | A | * | 6/1997 | Hens et al. | ..................... 75/228 |
| 5,682,665 | A | * | 11/1997 | Svanberg | ..................... 29/458 |
| 5,848,350 | A | * | 12/1998 | Bulger | ......................... 419/36 |
| 2005/0181328 | A1 | * | 8/2005 | Milne | .......................... 433/119 |
| 2005/0253301 | A1 | * | 11/2005 | Kraenzle | ................. 264/328.1 |

FOREIGN PATENT DOCUMENTS

| EP | 0 719 526 B1 | 7/1996 |
| JP | 09-168549 | 6/1997 |
| JP | 2003-164468 | 6/2003 |
| WO | WO 2004/108329 A1 | 12/2004 |

OTHER PUBLICATIONS

Randall M. German, "Powder Injection Molding," ASM Handbook, vol. 7 (1998), pp. 355-364.*
International Search Report dated Jul. 14, 2006.

* cited by examiner

*Primary Examiner*—Roy King
*Assistant Examiner*—Christopher Kessler
(74) *Attorney, Agent, or Firm*—KED & Associates, LLP

(57) ABSTRACT

The invention relates to a method for manufacturing a dental scaler tip using a powder injection molding process, a mould, and a scaler tip that is excellent in shape-reliability and injects fluid to a front end thereof along a curved section of the tip. The method comprises the steps of preparing feedstock and injecting the feed stock into a mould to form a molding body, wherein, the mould comprises an operating section to which cylindrical core pins having multi steps and an eccentric end formed at a front end thereof for forming the fluid passage is mounted; and a pair of slide cores disposed for supporting the eccentric ends of the core pins such that the slide cores face each other and are slid in the direction perpendicular to the movement direction of the core pins to form a cavity corresponding to a shape of an article to be formed.

13 Claims, 5 Drawing Sheets

[Fig. 1]
Conventional Art
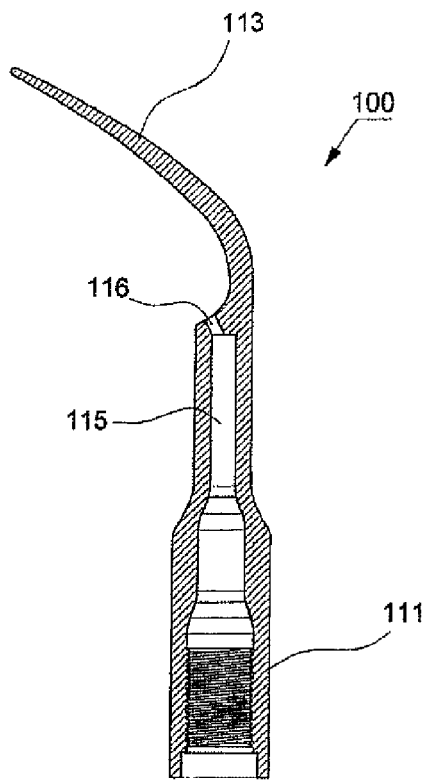
[Fig. 2]
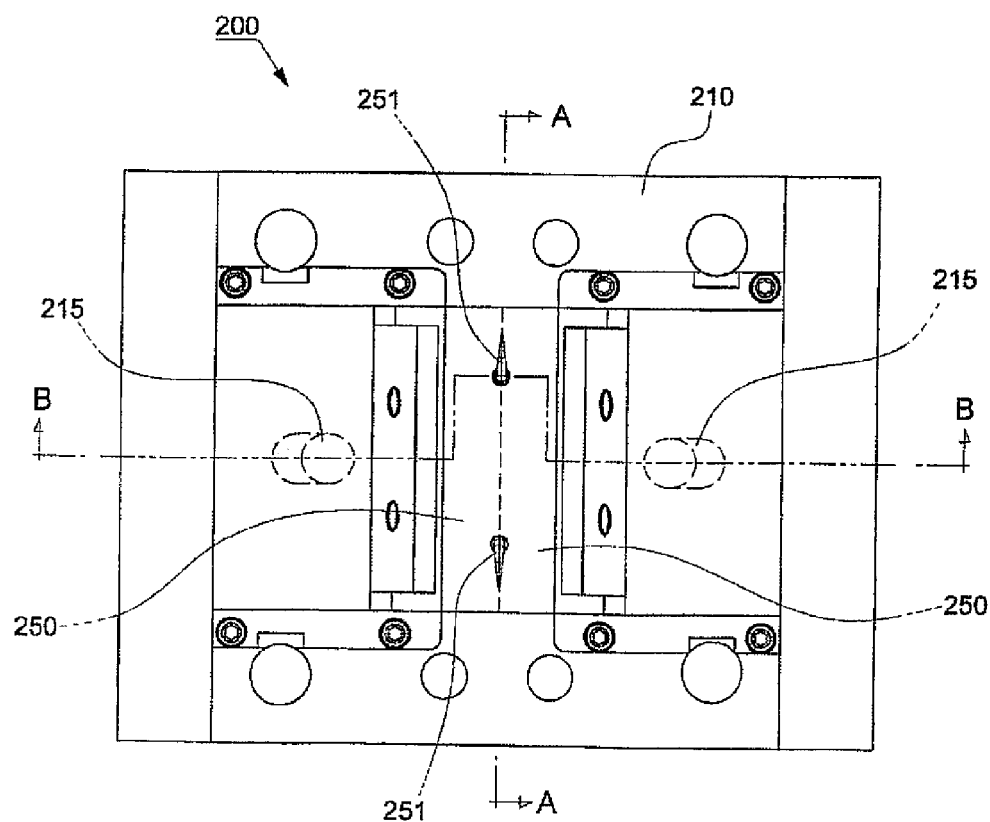

[Fig. 3]
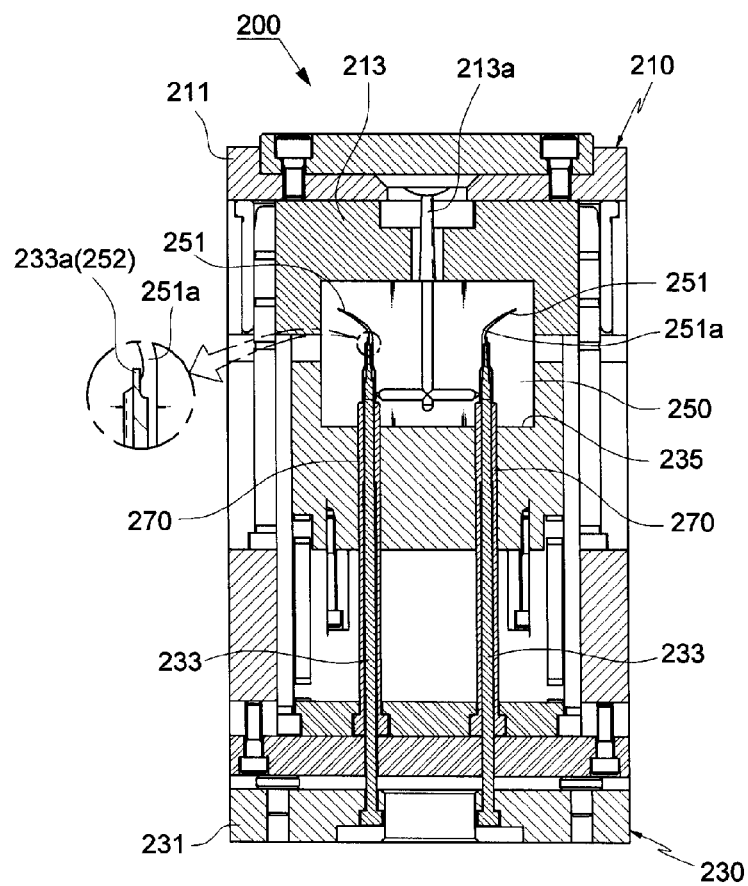
[Fig. 4]
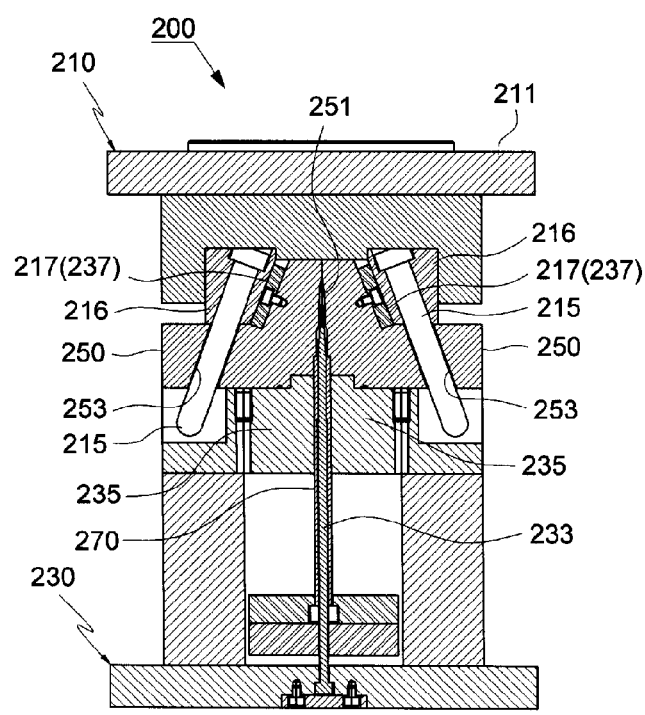

[Fig. 5]
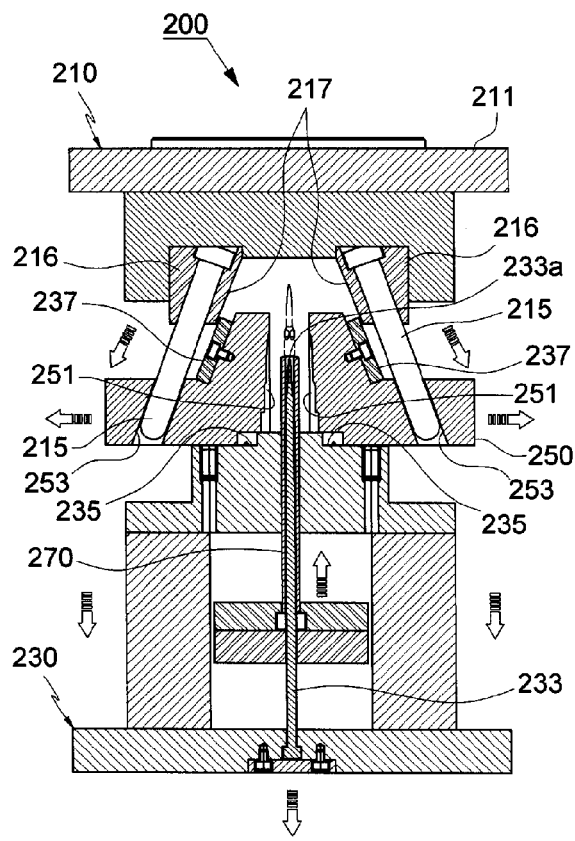
[Fig. 6]
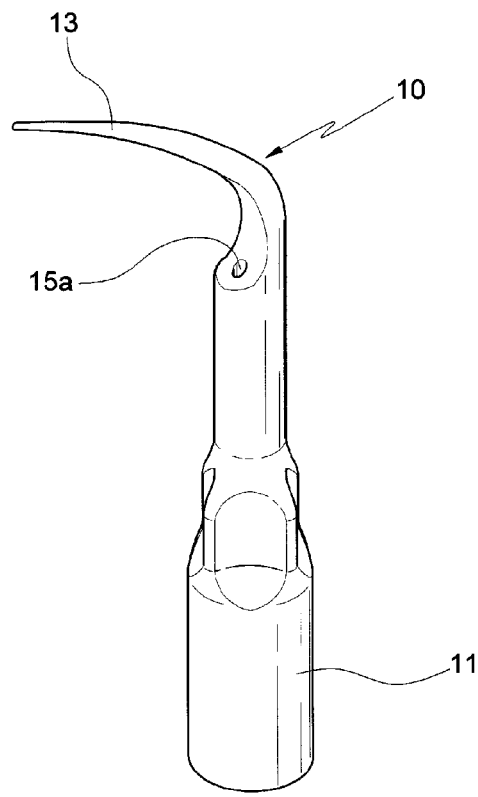

[Fig. 7]
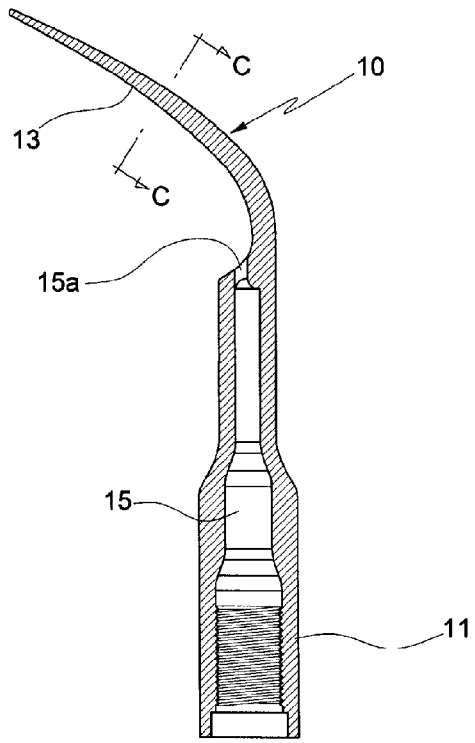
[Fig. 8]
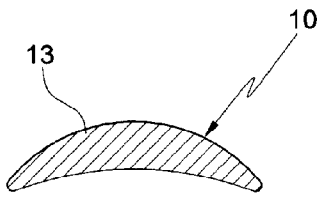
[Fig. 9]
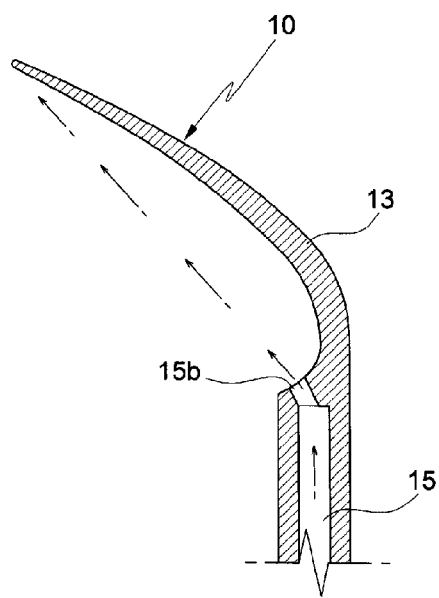

[Fig. 10]
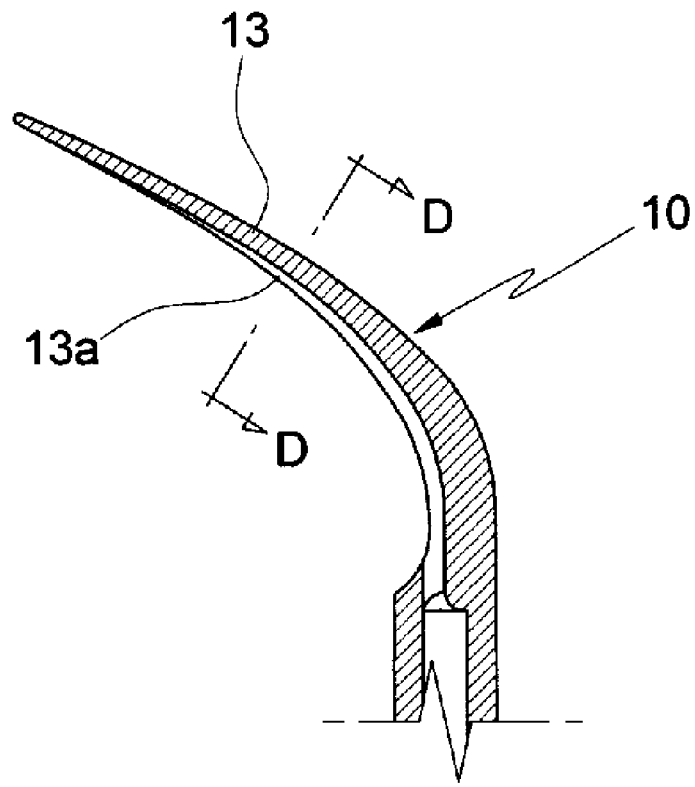
[Fig. 11]
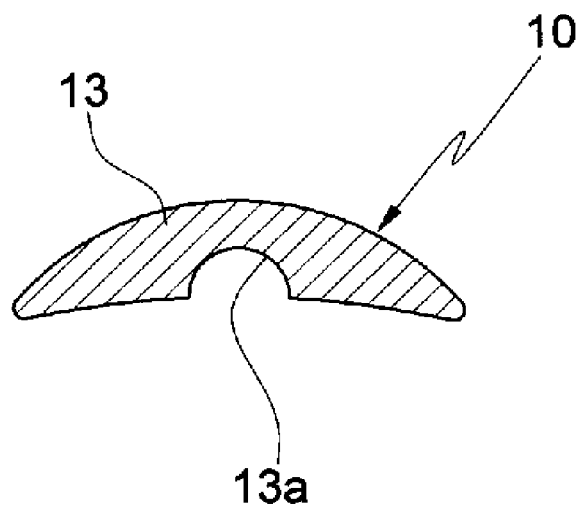

METHOD FOR MANUFACTURING DENTAL SCALER TIP USING POWDER INJECTION MOLDING PROCESS, MOLD USED THEREIN AND SCALER TIP MANUFACTURED BY THE SAME

TECHNICAL FIELD

The present invention relates to a dental scaler tip, more particularly to a method for manufacturing a dental scaler tip using a powder injection molding process which can produce the article in large quantities to save the manufacturing cost and forms an eccentric discharge port of a scaler tip to operate the mould using only one core pin, a mould used for the same that is provided with slide cores having the various shapes machined according to the article to enable the uniform article to be manufactured rapidly to enhance the characteristic and design of the article, and a scaler tip manufactured by the same that is more excellent in shape-reliability as compared with the conventional technique using the machining work and injects fluid to a front end thereof along a curved section of the tip section to perform effectively an operation.

BACKGROUND ART

A dental scaler has been used widely as a treatment instrument and an instrument which vibrates a tip mounted thereto using ultrasonic wave to remove dental calculus or other foreign substance deposited on teeth, and material for the scaler tip has a abrasion resistance requirement.

As shown in FIG. 1, the conventional scaler tip 100 consists of a coupling section 111 having a fluid passage 115 formed therein and used for injecting cleaning water or air and a curved shaped-tip section 113 extended and tapered gradually from the coupling section 111.

A screw section is formed at an entrance of the fluid passage 115 of the coupling section 111 for coupling the scaler tip to the equipment, a flat surface area is formed on an outer side of a fixing section for preventing the scaler tip from rotating in the state that the equipment and the scaler tip are coupled to each other, and a shape of front end portion of the tip section can be changed variously according to a purpose.

The scaler tip constructed as above is the small member with the entire length of approximately 30 mm or less and a maximum outer diameter of 4 mm or less. The scaler tip is used for crushing dental calculus using ultrasonic wave, separating crushed dental calculus from teeth and injecting cleaning water or air through the fluid passage 115 to expose well an area to be treated. To perform the above functions, it is desirable that cleaning water is smoothly injected toward a front end along a curved section of the scaler tip.

The scaler tip is manufactured by a the machining work method including a multiple cutting process for forming the fluid passage on an inside and outside of a working piece, a bending process for working the fluid passage using a jig and a polishing process for forming the tip section. And, a surface of the tip section is coated with titanium.

The conventional technique as described has the problems in that the small sized article having a difficulty in handling is manufactured through the machining working method consisting of the multiple processes so that the productivity becomes lower and a scrap and loss of material are increased due to a working characteristic of cutting process to increase a manufacturing cost.

Also, the conventional technique has the problems in that since the scaler tip is manufactured by the machining working, it is difficult to work the fluid passage with a small inner diameter to increase an error rate, an additional working process is required for forming the discharge port 116 having an inclined shape, and an accurate injection direction of cleaning water or air is not obtained unless the discharge is precisely worked to maintain a specific angle of the discharge port so that this discharge port can adversely affect the operation.

Also, since a surface of the article is coated, if the coating layer is peeled from the article or worn away, there is a doubt about a medical safety.

DISCLOSURE OF INVENTION

Technical Problem

The present invention is conceived to solve the aforementioned problems, an object of the present invention is to provide a method for manufacturing a dental scaler tip and a mould used in the same that, as compared with the conventional technique using the machining work, can form variously a shape of the scaler tip using a powder injection molding process to enhance a quality characteristic and design and can save a manufacturing cost through a mass production of articles having a complicated shape and abrasion resistance using powder mixture for the powder injection molding process obtained by mixing various kinds of powders.

Another object of the present invention is to provide a dental scaler tip that makes an injection of fluid direct to a front end portion of a tip section through an eccentric discharge port to achieve an effective injection.

Technical Solution

In order to achieve the above objects, a method for manufacturing a dental scaler tip consisting a coupling section mounted to the equipment and having a fluid passage formed therein and a curved shaped tip section extended from the coupling section, through a powder injection molding process, comprises the steps of preparing feedstock for injection by means of mixing raw material powder for the powder injection molding process containing titanium (Ti) or stainless steel with high molecular binder; and injecting the feed stock into a mould to form a molding body, wherein, the mould comprise an operating section to which cylindrical shaped core pins having multi steps and an eccentric end formed at a front end thereof for forming the fluid passage of the scaler tip is mounted; and a pair of slide cores disposed for supporting the eccentric ends of the core pins such that the slide cores face to each other and are slid in the direction perpendicular to the movement direction of the core pins to form a cavity corresponding to a shape of an article to be formed by an injecting process.

In general, the powder injection molding process in the present invention means a process including an injection molding process using powder mixture, a degreasing process and a sintering process.

In order to achieve the above object, a mould used for manufacturing a dental scaler tip which consists of a coupling section mounted to the equipment and having a fluid passage formed therein and a curved shaped tip section extended from the coupling section comprises a fixing section provided with a circular fixing plate on which a sprue is provided; an operating section having a guide table for slide cores and a circular operating plate corresponding to the fixing section and having cylindrical shaped core pins with multi steps and eccentric ends formed at a front end thereof for forming the fluid passage; a pair of slide cores disposed for supporting the eccentric ends of the core pins between the fixing section and the operating section such that the slide cores face to each other and are slid in the direction perpendicular to the movement direction of the core pins to form the cavity corresponding to a shape of an article to be formed by an injecting process; and pipe-shaped ejectors guiding a movement of the core pins and being moved upward below the article after the article is formed.

In order to achieve the above object, a dental scaler tip consisting of a coupling section mounted to the equipment and having a fluid passage formed therein and a curved shaped tip section extended from the coupling section characterized in that the scaler tip is formed by a powder injection molding process using the mould described above and a discharge port of the fluid passage is biased to one side from a center of the fluid passage.

ADVANTAGEOUS EFFECTS

In the method for manufacturing a dental scaler tip using the powder injection molding process and the mould used in the same according to the present invention, there are excellent effects that, as compared with the conventional technique using the machining work, the scaler tips having the various shapes can be formed, a quality characteristic and design can be enhanced by a rapid mould which can cope rapidly with a change of shape of the scaler tip and is suitable for manufacturing small batches of diverse scaler tips and the article can be manufactured in large quantities to save the manufacturing cost. Also, the design function such as an increase or decrease of abrasion resistance as an important requirement for the dental scaler tip can be added through a change of feedstock used in the powder injection molding process.

BRIEF DESCRIPTION OF THE DRAWINGS

The above and other objects, features and advantages of the present invention will become apparent from the following description of preferred embodiments given in conjunction with the accompanying drawings, in which:

FIG. 1 is a sectional view of the conventional dental scaler tip;

FIG. 2 is a plane view of a mould used for a powder injection molding process according to one embodiment of the present invention;

FIG. 3 is a sectional view taken along the line A-A in FIG. 2;

FIG. 4 is a sectional view taken along the line B-B in FIG. 2;

FIG. 5 is a state that the mould used for a powder injection molding process of FIG. 4 is operated;

FIG. 6 is a perspective view of a dental scaler tip according to the one embodiment of present invention;

FIG. 7 is a sectional view of FIG. 6;

FIG. 8 is a detailed sectional view taken along the line C-C in FIG. 7;

FIG. 9 is a sectional view of a scaler tip according to another embodiment of the present invention;

FIG. 10 is a sectional view of a scaler tip according to a further another embodiment of the present invention; and FIG. 11 is a detailed sectional view taken along the line D-D in FIG. 10.

BEST MODE FOR CARRYING OUT THE INVENTION

Reference will now be made in detail to a method for manufacturing a dental scaler tip using a powder injection molding process, a mold and a scaler tip of a preferred embodiment of the present invention, examples of which are illustrated in the accompanying drawings.

FIG. 2 is a plane view of a mould used for a powder injection molding process according to one embodiment of the present invention, FIG. 3 is a sectional view taken along the line A-A in FIG. 2, FIG. 4 is a sectional view taken along the line B-B in FIG. 2, and FIG. 5 is a state that the mould used for a powder injection molding process of FIG. 4 is operated.

In a method for manufacturing a dental scaler tip 10 consisting a coupling section 11 mounted to the equipment and having a fluid passage 15 formed therein and a curved shaped tip section 13 extended from the coupling section 11, the method for manufacturing a dental scaler tip according to the present invention using a powder injection molding process comprises the steps of preparing feedstock for injection by means of mixing raw material powder for the powder injection molding process containing titanium (Ti) or stainless steel with a high molecular weight binder; and injecting the feed stock into a mould 200 to form a molding body.

Here, the mould comprise an operating section 230 to which cylindrical shaped core pins 233 having multi steps and an eccentric end 233a formed at a front end thereof for forming the fluid passage 15 of the scaler tip 10 is mounted; a pair of slide cores 250 disposed for supporting the eccentric ends 233a of the core pins such that the slide cores face to each other and are slid in the direction perpendicular to the core pins to form a cavity corresponding to a shape of an article to be formed by an injecting process.

Undoubtedly, a degreasing process and a sintering process are then performed for the article obtained from the mould in the powder injecting mold process.

The above raw material powder contains stainless steel based-raw material powder or titanium based-raw material powder (STS316S, STS17-4H, Ti). If stainless steel based-raw material powder is used, a coating step can be additionally performed after completing the powder injection molding process, and in a case that titanium based-raw material powder is used, there is an advantage in that there is no need to perform the coating step. Conventional STS316L feedstock for the powder injection molding process is made by mixing powder composition of C of 0.3% or less, Cr of 16~18%, Ni of 10~13%, Si of 1% or less and the balance of Fe with high molecular binder. Also, conventional STS17-4PH feedstock for the powder injection molding process is made by mixing powder composition of C of 0.04~0.07%, Cr of 15~17%, Ni of 3~5%, Si of 1% or less, Mn of 3~5%, Nb of 0.15~0.45% and the balance of Fe with high molecular binder.

As described above, by manufacturing the scaler tip through the powder injection molding process, as compared with the conventional technique using the machining work, the article having more various shape and uniform quality can be embodied, and so it is possible to enhance a function and design of the scaler tip.

As compared with the machining work, the powder injection molding process is advantageous in that an use efficiency of material is high, a mass production of the article (scaler tip) can be achieved so that the productivity is remarkably enhanced and the scaler tips with various shapes can be manufactured freely by using the slide cores having the various shaped tip sections which are variously machined. And, by employing the powder injection molding process of the present invention, a high abrasion resistance which is one of the requirements for the dental scaler tip can be substantially obtained.

As shown in FIG. 2 to FIG. 5, the mould 200 according to the present invention used in the powder injection molding process for manufacturing the dental scaler tip 10 which consists of the coupling section 11 mounted to the equipment and having the fluid passage 15 formed therein and the curved shaped tip section 13 extended from the coupling section 11 comprises a fixing section 210 provided with a circular fixing plate 21 ion which a sprue 213 is provided; the operating section 230 having a guide table 235 for the slide cores 250 and a circular operating plate 231 corresponding to the fixing section 210 and having the cylindrical shaped core pins 233 with multi steps and the eccentric ends 233a formed at a front end thereof for forming the fluid passage 15; a pair of slide cores 250 disposed for supporting the eccentric ends 233a of the core pins between the fixing section 210 and the operating section 230 such that the slide cores face to each other and are slid in the direction perpendicular to a movement direction of the core pins to form the cavity 251 corresponding to a shape of an article to be formed by an injecting process and pipe-shaped ejectors 270 guiding a movement of the core pins 233 and being moved upward below the article after the article is formed.

Here, the eccentric end 233a has a small diameter of approximately 0.6 mm or less and an front end is protruded out of the molding body so that there is an enormous risk of damage of the eccentric end. Accordingly, there is need to have a structure that can grasp the eccentric end and to guide an injection direction of discharged fluid. To achieve the above purposes, the eccentric end 233a of each core pin used for forming a discharge port 15a of the fluid passage in the scaler tip is formed such that the eccentric end is not coincided with, but deviated from a central line of the fluid passage 15. Also, the above structure has the advantage in that, only one core pin is formed for forming the discharge port by forming the eccentric core pin of the mould, and so a structure of the mold can be simplified and a manufacturing cost can be saved significantly and the core pin 233 can be replaced with new one when the mould is repaired.

Here, a grasping section 252 grasping an end portion of the core pin is formed concavely on each slide core 250 along a cavity 251, and there is need to form a space acting as a support section between the grasping section 252 grasping an end portion of the core pin and a curved section 251a of the cavity for preserving the grasping section 252.

Also, the fixing section 210 is installed at an upper side, the operating section 230 is installed at a lower side such that the core pins 233 are disposed vertically, and angular pins 215 are slantly installed at the fixing section 210 and face each other at both sides of the core pins 233 for guiding a horizontal movement of the slide cores 250. The slide cores 250 are installed on the guide table 235 of the operating section 230, and it is preferable that angular passages 253 corresponding to the angular pins 215 are formed at the slide cores 250, respectively, so that each angular pin 215 is received in the corresponding angular passage 253.

Angular guide surfaces 217 having the slope which is the same as that of the angular pins are formed above the angular pins 215, respectively, and it is desirable that angular slide surfaces 237 corresponding to the angular guide surfaces are formed on the slide cores 250, respectively.

The angular guide surfaces 217 are formed on one surface of angular pin supporting blocks 216, respectively, and the angular slide surfaces 217 are formed integrally with one side of the corresponding slide cores 250 or can be formed on additional members fixed to the slide cores 250, respectively.

In the present invention constructed above, the basic requirements for the scaler tip, such as a preservation of thickness of the coupling section coupled with the equipment for machine-working, a sectional shape for preventing a rotation when the scaler tip is combined with the equipment, a smooth supply of fluid such as cleaning water, an injection of fluid to an area on which a treatment is performing, that is, a front end of the tip section, are satisfied by a design of the slide cores 250 and the core pins 233.

Also, since it is possible to replace the slide cores 250 in which the cavity 251 is formed, if a design of the article is modified, only the slice cores 250 are replaced simply with new one so that the articles with the various shapes can be manufactured through only one mould. Accordingly, the present invention can embody the mould that can cope rapidly with a change of shape of the scaler tip and has the structure which is suitable for manufacturing small batches of diverse scaler tips.

Below, an operation of the mould 200 according to the present invention constructed above is described reference to FIG. 4 and FIG. 5. When the injection molding process is carried out, an injection is safely performed in a state that the both slide cores 250 grasp protrusions of the eccentric ends 233a (which are placed at an outside of the molding body) of the core pins in the operating section 230 at both sides.

Also, when the molding body is drawing out, while the operating section 230 is moved downward, the core pins 233 are separated from the fixing section 230. Simultaneously, the slide cores 250 disposed on the guide table 235 of the operating section are horizontally moved by the angular pins 215 combined therewith. Consequently, the slide cores are diagonally moved to an outside.

That is, the slide cores 250 which face each other at both sides are cooperated closely with a vertically movement of the operating section 230 with respect to the fixing section 210, and so an opening/closing of the cavity 251 and the grasping sections 252 grasping end portions of the core pins is automatically performed. Accordingly, the And, the core pins 233 are fixed to the circular operating plate 231 and receive the uniform force at the time of moving downward due to a movement of the circular operating plate, while the ejectors 270 push the articles at a lower side, and so the articles are safely extracted without generating any scratch on the surface of the articles.

As shown in FIG. 6 and FIG. 7, in the scaler tip 10 according to the present invention manufactured by the powder injection molding process and the mold therefore and comprising the coupling section 11 mounted to the equipment and having the fluid passage 15 formed therein and the curved shaped tip section 13 extended from the coupling section 11, the scaler tip is manufactured by powder injection molding process using the mould 200 as described above and the discharge port 15a of the fluid passage is biased to one side from a center of the fluid passage.

The eccentric discharge port 15a makes the fluid flow smoothly to the front end along a curved section of the tip section to guide the injection guide of the discharged fluid to the front end of the tip section, and so a more effective injection is achieved.

The scaler tip 10 according to the present invention is made of titanium based-raw material powder, and so the scaler tip constructed and manufactured as above can be used semipermanently due to strong abrasion resistance.

As shown in FIG. 8, a discharge port 15b of the fluid passage can be formed slantly such that the discharge port is directed to an end of the tip section. However, there is the problem in that an additional core pin should be provided in the mould to obtain the above structure.

Further, as shown in FIG. 8, it is desirable that the tip section 13 have a curved shape in section.

Also, as shown in FIG. 10 and FIG. 11, a guide groove 13a can be formed on the tip section 13 for guiding the discharged water to an inner side.

In a case of forming the guide groove 13a, an additional core pin should be provided in the mould.

As described above, in the scaler tip manufactured by the powder injection molding process according to the present invention, a curvature of the tip section and the various designs such of the front end portion such as gentle, blunt, jagged and sharpen shapes can be embodied easily.

INDUSTRIAL APPLICABILITY

While the present invention has been described and illustrated herein with reference to the preferred embodiment thereof, it will be apparent to those skilled in the art that various modifications and variations can be made therein without departing from the spirit and scope of the invention. Thus, it is intended that the present invention covers the modifications and variations of this invention that come within the scope of the appended claims and their equivalents.

As described above, in the method for manufacturing a dental scaler tip using the powder injection molding process and the mould used in the same according to the present invention, there are excellent effects that, as compared with the conventional technique using the machining work, the scaler tips having the various shapes can be formed, a quality characteristic and design can be enhanced by a rapid mould which can cope rapidly with a change of shape of the scaler tip and is suitable for manufacturing small batches of diverse scaler tips and the article can be manufactured in large quantities to save the manufacturing cost. Also, the design function such as an increase or decrease of abrasion resistance as an important requirement for the dental scaler tip can be added through a change of feedstock used in the powder injection molding process.

The invention claimed is:

1. A method for manufacturing a dental scaler tip, the dental scaler tip comprising a coupling section having a fluid passage formed therein and a curved tip section that extends from the coupling section, the method comprising:
    mixing a raw material powder containing titanium (Ti) or stainless steel combined with a binder to prepare feedstock;
    injecting the prepared feedstock into a mould so as to form at least one mould body at at least one corresponding core pin provided in the mould, the at least one corresponding core pin having multiple steps formed thereon and an eccentric distal end so as to form the fluid passage of the scaler tip;
    moving an operating plate of the mould in a first direction away from a fixing plate of the mould so as to move first and second slide cores of the mould in a second direction away from each other and remove the at least one core pin from the at least one mould body; and
    ejecting the at least one mould body from the mould.

2. The method as claimed in claim 1, further comprising:
    coating the at least one mould body with titanium if the raw material powder does not contain titanium.

3. The method as claimed in claim 1, wherein the at least one core pin comprises a plurality of core pins, and wherein the mould further comprises: a guide table on which the first and second slide cores are positioned so as to support the eccentric ends of the core pins, wherein the first and second slide cores face each other so as to form a cavity therebetween corresponding to a shape of an article to be formed by an injecting process in the mould.

4. The method as claimed in claim 3, wherein the first and second slide cores slide in a direction perpendicular to a movement direction of the core pins and the operating plate to which the core pins are mounted so as to open and close the cavity.

5. The method as claimed in claim 4, wherein ejecting the at least one mould body comprises moving the operating plate downward so as to move the first and second slide cores outward, away from each other and open the cavity.

6. The method as claimed in claim 5, wherein ejecting the at least one mould body comprises moving an ejector positioned below the at least one mould body upward and a guiding corresponding movement of the core pins.

7. The method as claimed in claim 6, wherein the mould further comprises:
    angular pins installed at a slant through the first and second slide cores and positioned outward from the core pins; and
    angular passages formed in the first and second slide cores so as to receive the angular pins therein such that the angular pins guide a horizontal movement of the first and second slide cores as the operating plate moves vertically.

8. The method as claimed in claim 1, wherein injecting the prepared feedstock into a mould further comprises forming a coupling section having a fluid passage formed therein and a curved tip section that extends from the coupling section.

9. The method as claimed in claim 8, wherein forming a coupling section having a fluid passage formed therein further comprises forming a discharge port at an outlet end of the fluid passage that is offset from a center of the fluid passage.

10. The method as claimed in claim 9, wherein forming a discharge port at an outlet end of the fluid passage comprises forming the discharge port at an incline with respect to a central axis of the fluid passage such that the discharge port is oriented toward a distal end of the tip section.

11. The method as claimed in claim 8, wherein forming a curved tip section that extends from the coupling section comprises forming a curved tip section having a curved cross section.

12. The method as claimed in claim 8, wherein forming a curved tip section that extends from the coupling section further comprises forming a guide groove in the tip section that is in fluid communication with the fluid passage.

13. The method as claimed in claim 1, wherein moving an operating plate in a first direction and first and second core sections in a second direction comprises moving the first and second core sections in the second direction that is perpendicular to the first direction so as to open a cavity defined therebetween.

* * * * *